US006704588B2

(12) United States Patent
Ansari et al.

(10) Patent No.: US 6,704,588 B2
(45) Date of Patent: Mar. 9, 2004

(54) METHOD AND APPARATUS FOR THE NON-INVASIVE MEASUREMENT OF BLOOD GLUCOSE LEVELS IN HUMANS

(76) Inventors: Rafat R. Ansari, 3283 N. Sandy La., Avon, OH (US) 44011; Luigi Rovati, Montello 57, I25128, Brescia (IT)

( * ) Notice: Subject to any disclaimer, the term of this patent is extended or adjusted under 35 U.S.C. 154(b) by 0 days.

(21) Appl. No.: 10/172,258

(22) Filed: Jun. 14, 2002

(65) Prior Publication Data

US 2003/0233036 A1 Dec. 18, 2003

Related U.S. Application Data

(60) Provisional application No. 60/298,766, filed on Jun. 16, 2001.

(51) Int. Cl.$^7$ .................................................. A61B 5/00
(52) U.S. Cl. ...................................................... 600/319
(58) Field of Search ................................ 600/310, 316, 600/318, 319, 321

(56) References Cited

U.S. PATENT DOCUMENTS

| | | | |
|---|---|---|---|
| 3,958,560 | A | 5/1976 | March |
| 3,963,019 | A | 6/1976 | Quandt |
| 5,028,787 | A | 7/1991 | Rosenthal et al. |
| 5,209,231 | A | 5/1993 | Cote et al. |
| 5,243,983 | A | 9/1993 | Tarr et al. |
| 5,398,681 | A | 3/1995 | Kupershmidt |
| 5,433,197 | A | 7/1995 | Stark |
| 5,448,992 | A | 9/1995 | Kupershmidt |
| 5,535,743 | A | 7/1996 | Backhaus et al. |
| 5,560,356 | A | 10/1996 | Peyman |
| 5,713,353 | A | 2/1998 | Castano |
| 5,835,215 | A | 11/1998 | Toida et al. |
| 5,896,198 | A | 4/1999 | Chou et al. |
| 5,969,815 | A | 10/1999 | Toida et al. |
| 5,971,922 | A | 10/1999 | Arita et al. |
| 6,370,407 | B1 | 4/2002 | Kroeger et al. |

FOREIGN PATENT DOCUMENTS

| | | |
|---|---|---|
| JP | 9-299333 | 11/1997 |
| JP | 11-244243 | 9/1999 |
| WO | PCT/US99/05007 | 3/1999 |

OTHER PUBLICATIONS

Justin S. Baba et al.,. "Dual–detector Polarimetry for Compensation of Motion Artifact in a Glucose Sensing System", SPIEWeb, pp. 1–5, 2002.

Luigi L. Rovati et al., "A Theoretical Analysis of a New Polarimetric Optical Scheme for Glucose Sensing in the Human Eye", NASA Glenn Research Center, Optics Letters, pp. 1–14, Apr. 2002.

Rjafat R. Ansari et al., "A New Optical Scheme for a Polarimetric–Based Glucose Sensor", pp. 1–27, Apr. 2002.

Brent D. Camerson et al., "The Use of Polarized Laser Light Through the Eye for Noninvasive Glucose Monitoring", in *Diabetes Technology&Therapeutics*, vol.#2, 1999 (Mary Ann Liebert, Inc.), pp. 135–143.

Roger J. McNichols et al., "Optical glucose sensing in biological fluids: an overview", Journal of Biomedical Optics vol. 5 #1 pp. 5–16, Jan. 2000.

*Primary Examiner*—Eric F. Winakur
(74) *Attorney, Agent, or Firm*—Fay, Sharpe, Fagan, Minnich & McKee, LLP

(57) ABSTRACT

An apparatus (10) for determining a diagnostic glucose level in a human subject includes a light source (30) that produces collimated light at a selected wavelength. The collimated light is arranged such that it passes through a portion of an eye (12) of the subject and reflects off an eye lens (16) at a selected angle ($\theta_B$) as reflected light. A polarization analyzer (70) measures a polarization of the reflected light that exits the eye (12). A path length processor (68) determines an optical path length ($L_\lambda$) of the reflected light within an aqueous humor (22) of the eye (12). A glucose level processor (90) computes a glucose concentration based on the measured polarization and the determined optical path length ($L_\lambda$).

21 Claims, 9 Drawing Sheets

METHOD AND APPARATUS FOR THE NON-INVASIVE MEASUREMENT OF BLOOD GLUCOSE LEVELS IN HUMANS

This application claims the benefit of U.S. Provisional Application Ser. No.60/298,766 of inventors Rafat R. Ansari and Luigi Rovati, entitled "Method and Apparatus for the Non-Invasive Measurements of Blood-Glucose Levels in Humans", filed on Jun. 16, 2001.

BACKGROUND OF THE INVENTION

The present invention relates to the medical arts. It particularly relates to the measurement of a diagnostic glucose level in a human subject, especially for the monitoring of diabetic patients, and will be described with particular reference thereto. However, the invention will also find application in conjunction with the non-invasive measurement of concentrations of other proteins and other optically active substances in the human body for medical diagnosis and monitoring. For example, the invention is contemplated to be applied for measuring β-amyloid protein concentrations in the body, which are indicative of Alzheimer's disease.

Diabetes is presently the fourth leading cause of mortality in the United States. Diabetes can lead to severe complications over time, including blindness, renal and cardiovascular diseases, and peripheral neuropathy associated with limbs. Diabetics typically exhibit poor blood circulation in lower extremities of the body which can lead to gangrene and subsequent amputation.

These and other diabetic complications can typically be minimized or avoided by suitable medical intervention. In the case of diabetes mellitus which relates to inadequate insulin production by the body, a regular administration of insulin injections helps convert glucose to glycogen to control diabetic symptoms and complications. The insulin-injection therapy is preferably closely monitored by frequently measuring diagnostic glucose levels. In a usual approach, blood is drawn and the serum glucose level is measured. Since this monitoring should be done regularly, e.g. on a daily basis, it is preferably self-administered, typically using a finger-prick blood extraction.

A problem arises because diabetic patients are reluctant to perform regular glucose monitoring by painful blood extraction. Blood extraction can also produce infections or introduce harmful contaminants into the body. For these and other reasons, patients sometimes neglect the invasive glucose self-monitoring and fail to adjust their insulin intake to accommodate changes and variations in glucose level. Hence, there is a continuing need for an improved and preferably non-invasive glucose monitoring method and apparatus which conveniently measures a diagnostic glucose level in the human body.

A number of approaches have been developed for determining the glucose level in ocular tissue. In particular, the glucose concentration in the aqueous humor of the eye closely mimics glucose levels in the blood. Furthermore, glucose is an optically active material whose concentration in an aqueous solution can be measured by optical polarimetric methods.

U.S. Pat. No. 5,209,231 issued to Cote et al., U.S. Pat. No. 5,560,356 issued to Peyman, and U.S. Pat. No. 6,370,407 issued to Kroeger et al. are exemplary of recent efforts to exploit the optical activity of glucose in the aqueous humor to monitor a diagnostic glucose level. However, there remains a need in the art for an improved non-invasive diagnostic glucose monitoring which is convenient for diabetic patients to use, does not require ocular implants or refractive index-matching material, provides automatic corrections for individual variations in ocular geometry and optical properties, and is optically robust and substantially insensitive to minor deviations from the designed optical alignment or configuration.

The present invention contemplates an improved apparatus and method which overcomes the aforementioned limitations and others.

SUMMARY OF THE INVENTION

According to one aspect of the invention, a method is provided for determining a diagnostic glucose level for a person. Light is reflected off an ocular lens at a Brewster's angle. A polarization rotation of the reflected light is measured after exiting the eye. A glucose concentration is determined based on the measured polarization rotation.

According to another aspect of the invention, a method is provided for determining a diagnostic glucose level. Light is reflected from an internal ocular interface at an incident angle that has a selected reflection polarization characteristic. A polarimetric parameter of the reflected light is measured. A glucose concentration is computed based on the polarimetric parameter.

According to yet another aspect of the invention, an apparatus is disclosed for determining a diagnostic glucose level in a human subject. A light source produces collimated light at a selected wavelength. The collimated light is arranged such that the collimated light passes through a portion of an eye of the subject and reflects off an eye lens at a selected angle as reflected light. A polarization analyzer measures a polarization of the reflected light that exits the eye. A path length processor determines an optical path length of the reflected light within an aqueous humor of the eye. A glucose level processor computes a glucose concentration based on the measured polarization and the determined optical path length.

One advantage of the present invention resides in providing convenient and robust non-invasive monitoring of blood glucose levels for calibrating insulin injections or other medical treatment of the diabetic condition.

Another advantage of the present invention resides in improved accuracy and precision in non-invasive measurement of glucose concentration in the human body.

Yet another advantage of the present invention resides in providing a painless method and apparatus for monitoring glucose levels in diabetic patients.

Numerous additional advantages and benefits of the present invention will become apparent to those of ordinary skill in the art upon reading the following detailed description of the preferred embodiment.

BRIEF DESCRIPTION OF THE DRAWINGS

The invention may take form in various components and arrangements of components, and in various steps and arrangements of steps. The drawings are only for the purpose of illustrating preferred embodiments and are not to be construed as limiting the invention.

DETAILED DESCRIPTION OF THE PREFERRED EMBODIMENTS

Figure 1:
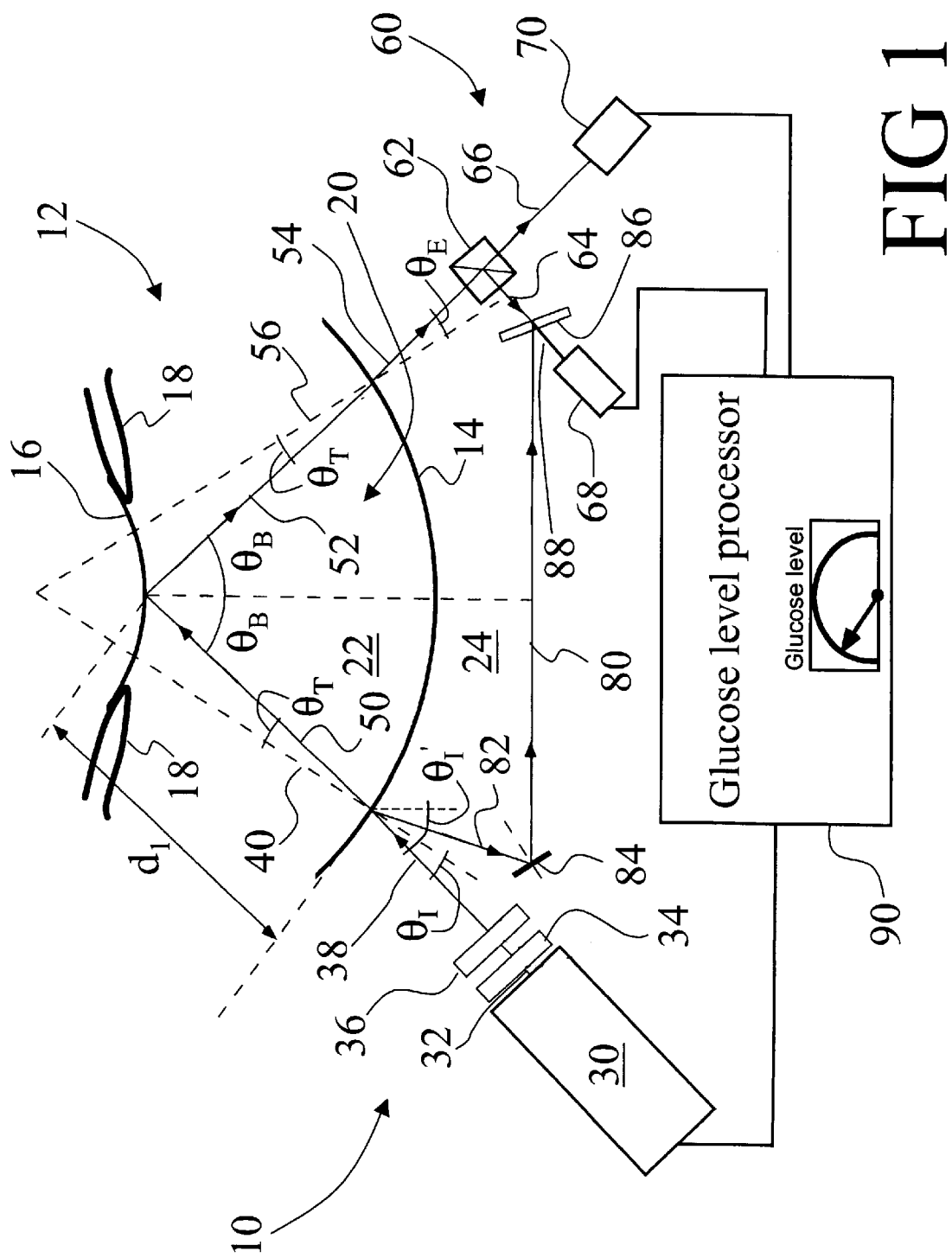
FIG. 1 schematically shows an apparatus for monitoring a diagnostic glucose level in accordance with one embodiment of the invention.

With reference to FIG. 1, a glucose monitoring apparatus 10 monitors an eye 12 which includes, among other ocular tissues, a cornea 14, a lens 16, and an iris 18, which cooperate to define an anterior chamber 20 that is filled with a fluid called the aqueous humor 22. The aqueous humor includes a concentration of glucose which is to be measured.

The light-transmissive ocular tissues, in particular the cornea 14, the lens 16, and the aqueous humor 22, are each optically characterized by a refractive index denoted by "n". Suitable refractive indices include $n_c$=1.336, $n_l$=1.4208, and $n_h$=1.336, for the cornea 14, the lens 16, and the aqueous humor 22, respectively. Although in this simplified model $n_c$=$n_h$, it is also contemplated that more precise and perhaps different refractive index values can be employed. An ambient air 24 is suitably characterized by $n_a$=1.00.

With continuing reference to FIG. 1, the apparatus 10 includes a light source 30 that produces substantially collimated light 32. The light source 30 is preferably a multiple-wavelength light source. In FIG. 1, a multi-wavelength laser is employed. However, it is also contemplated to use other light sources that produce light at a plurality of wavelengths, such as: a white light source coupled with an optical collimator and one or more wavelength-selective filters; a mercury, sodium, or other type of arc discharge lamp; one or more light emitting diodes (LEDs); and the like. Because the light impinges upon the human eye, it should have an intensity comporting with eye safety guidelines, such as those promulgated by the American National Standards Institute (ANSI Report No. Z136.1).

The light 32 is optionally selectively polarized, e.g. using a linear polarizer 34 in combination with a quarter-wave (λ/4) retarder 36 to produce a circularly polarized light 38 which impinges upon the cornea 14 at an incident angle $θ_I$ referenced to a normal 40 to the local cornea surface. (Unless otherwise noted, angles cited herein are referenced to an interface or surface normal, i.e. the normal is designated as 0°).

The light 38 passes through the cornea 14 and into the aqueous humor 22 to form a transmitted light 50. The light is refracted at the tissue interfaces so that the transmitted light 50 is traveling at a transmitted angle $θ_T$ relative to the surface of the cornea 14 through which the light passes. The angular change from $θ_I$ to $θ_T$ is calculable using Snell's Law according to:

$$n_1 \sin θ_1 = n_2 \sin θ_2 \qquad (1)$$

where the subscripts "1" and "2" refer to the incident and transmitted sides of the refracting interface. The transmitted light 50 impinges on the lens 16, where a portion of the light is reflected to form a reflected light 52.

The incident angle $θ_I$ is selected such that after refraction at the ambient/cornea and cornea/aqueous humor interfaces the transmitted light 50 impinges upon the lens 16 at a Brewster's angle $θ_B$. Those skilled in the art will recognize that the Brewster's angle, also known as the polarizing angle, is a special angle at which the light polarization component in the plane of incidence (i.e., the p-polarization) is extinguished upon reflection, such that the reflected light is substantially polarized out of the plane of incidence, i.e., s-polarized. The s- and p-polarizations are defined with respect to the plane of incidence which contains the incident beam 50 and the reflected beam 52. The Brewster's angle for the aqueous humor/lens interface is given by:

$$θ_B = \arctan\left(\frac{n_1}{n_h}\right) = \arctan\left(\frac{1.4208}{1.336}\right) = 46.76° \qquad (2)$$

Because of the special polarizing properties of the Brewster's angle $θ_B$ reflection, the reflected light 52 is linearly polarized, and more particularly s-polarized.

Although in the embodiment described herein a reflection at the Brewster's angle of the aqueous humor/lens interface is employed, it is also contemplated to employ reflections at other angles and/or ocular interfaces which have known polarizing properties. For example, a reflection at the lens/vitreous humor interface at the critical angle of that interface is also contemplated. Those skilled in the art recognize the critical angle as the smallest angle at which light traveling from an optically denser medium (e.g., the lens) toward a less dense medium (e.g., the vitreous humor lying behind the lens in the eye) experiences total reflection.

The reflected beam 52 traverses the aqueous humor 22. Because the aqueous humor contains substantial concentrations of glucose and other optically active substances, the polarization rotates away from the s-polarization. The rotation is given by:

$$α_λ = L_λ \sum_i ([α]^T_{λ,pH,i} c_i) \qquad (3)$$

where $α_λ$ is the polarization rotation at the wavelength λ of the reflected light, the index i goes over all significant optically active substances including at least glucose, $[α]^T_{λ,pH,i}$ is a specific rotation of the ith substance at the wavelength λ, $c_i$ is the concentration of the ith substance, and $L_λ$ is an optical path length. For a symmetric reflection geometry relative to a center of the lens 16, the physical path $d_1$ of the transmitted light 50 is equal to the physical path of the reflected light 52, and the optical path length of the reflected light 52 is given by ($n_h × d_1$) where $n_h$ is the refractive index of the aqueous humor.

The reflected light 52 impinges upon the aqueous humor/cornea and the cornea/ambient interfaces, where the light is refracted to form exiting light 54 directed outwardly from the cornea at an exit angle $θ_E$ relative to a normal 56 to the local cornea surface. For the symmetric geometry shown in FIG. 1, the exiting angle $θ_E$ equals the incident angle $θ_I$.

Asymmetric geometries respective to the center of the lens 16 can also be employed, for which the incident angle $\theta_I$ and the exiting angle $\theta_E$ are typically somewhat different.

The exiting light 54 is characterized by analyzing optics 60. A beam-splitter 62 splits the exiting light 54 into first and second beams 64, 66. The first beam 64 is analyzed by a path length detector, such as a low-coherence interferometric detector 68 which extracts the optical path length, while the second beam 66 is analyzed by a polarization analyzer or detector 70. The polarization analyzer 70 preferably extracts amplitude and phase information for both the p-polarization component and the s-polarization component of the second beam 66, e.g. in a Jones matrix or other suitable format.

The low-coherence interferometric detector 68 employs a reference beam 80 obtained from a reflected light component 82 that reflects back into the ambient 24 when the incident beam 38 impinges upon the cornea 14. The reference beam 80 is obtained using suitable optical components, such as a mirror 84 and a second beam splitter 86, to produce a combined light 88 that is analyzed by the low-coherence interferometric detector 68. For the symmetric geometry relative to the center of the lens 16 shown in FIG. 1, the low-coherence interferometric detector 68 measures an optical path length of $(2 \times n_h \times d_1)$ corresponding to a sum of the paths of the transmitted light 50 and the reflected light 52.

A variation in optical path length of about 5 percent due to eye movement and about 10 percent between individuals is expected. Measurement of the optical path length, e.g. using the low-coherence interferometric detector 68, is preferably performed to correct for such variations. However, it is also contemplated to omit the optical path length measurement and use an estimated optical path length based on the ocular geometry.

A glucose level processor 90 computes a polarization rotation $\alpha$ and an optical path length $L_\lambda$ from measurements of the analyzing optics 60. The exiting light 54 is related to the incident light 38 according to:

$$E_{exit} = T_2 \, T_g \, R_B \, T_g \, T_1 \, E_{inc} \quad (4)$$

where $E_{inc}$ is the incident beam 38 represented as a Jones vector, $T_1$ is the Jones matrix for transmission from the ambient 24 into the aqueous humor 22 through the air/cornea/aqueous humor interface, the rightmost $T_g$ is the Jones matrix for transmission through the aqueous humor 22 from the cornea 14 to the lens 16, $R_B$ is the Jones matrix for reflection at the lens 16, the leftmost $T_g$ is the Jones matrix for transmission through the aqueous humor 22 from the lens 16 to the cornea 14 (the leftmost and rightmost $T_g$ matrices are equivalent for the symmetric reflection geometry of FIG. 1), $T_2$ is the Jones matrix for transmission from the aqueous humor 22 to the ambient 24 through the aqueous humor/cornea/air interface, and $E_{exit}$ is the exiting beam 54.

For the exemplary refractive indices given previously in which $n_c = n_h$ (aqueous humor having the same refractive index as the cornea), the Jones matrices are given by:

$$T_1 = \begin{bmatrix} \frac{2\sin(\theta_T)\cos(\theta_1)}{\sin(\theta_T + \theta_1)\cos(\theta_1 - \theta_T)} & 0 \\ 0 & \frac{2\sin(\theta_T)\cos(\theta_1)}{\sin(\theta_T + \theta_1)} \end{bmatrix} \quad (5),$$

$$T_g = \begin{bmatrix} \cos(\alpha_\lambda) & \sin(\alpha_\lambda) \\ -\sin(\alpha_\lambda) & \cos(\alpha_\lambda) \end{bmatrix} \quad (6),$$

$$R_B = \begin{bmatrix} 0 & 0 \\ 0 & -\sin(2\theta_B - 90°) \end{bmatrix} \text{ and} \quad (7),$$

$$T_2 = \begin{bmatrix} \frac{2\sin(\theta_T)\cos(\theta_E)}{\sin(\theta_E + \theta_T)\cos(\theta_E - \theta_T)} & 0 \\ 0 & \frac{2\sin(\theta_T)\cos(\theta_E)}{\sin(\theta_E + \theta_1)} \end{bmatrix} \quad (8),$$

where the angles $\theta_I$, $\theta_B$, and $\theta_E$ are as shown in FIG. 1 and $\alpha_\lambda$ is expressed in equation (3). The incident light 38 is described by a Jones vector of the form:

$$\vec{E}_{inc} = \begin{pmatrix} E_{0x} e^{j(\omega t - kz)} \\ E_{0y} e^{j(\omega t - kz)} \end{pmatrix} = \frac{1}{\sqrt{2}} \begin{pmatrix} 1 \\ j \end{pmatrix} \quad (9),$$

where $E_{0x}$ and $E_{0y}$ are the amplitudes of the x- and y-components of the electric field $\vec{E}_{inc}$, and $(\omega t - kz)$ designates the spatial and temporal variation of the electric fields. The right-hand side of equation (9) is appropriate for a circularly polarized incident light.

The Brewster's or polarizing angle $\theta_B$ is expressed in equation (2) as a function of the refractive index of the aqueous humor ($n_h$) and the lens ($n_1$), and the incident angle $\theta_I$ can be computed using Snell's Law (equation (1)) based upon the Brewster's angle $\theta_B$ and knowledge of the ocular geometry. A suitable ocular geometric model is the Le Grand ocular model, for example as described in W. Lotmar, Journal of the Optical Society of America, volume 61, pages 1522–1529 (1971). The exiting angle $\theta_E$ can be computed similarly to $\theta_I$.

Those skilled in the art can readily modify the expressions of equations (4)–(9) to incorporate a different incident light angle, different incident light polarization (e.g., s-polarized light), to account for a difference in refractive index between the cornea ($n_c$) and the aqueous humor ($n_h$), to account for refraction during transmission through the cornea 14, to account for ocular geometry variations in individual patients, and the like.

In one suitable embodiment, the glucose level processor 90 solves equation (4) based on the computed angles $\theta_I$, $\theta_B$, and $\theta_E$, parameters of the selected polarization of the incident light 38, and the polarization of the exiting light 54 as measured by the polarization detector 70, to obtain the polarization rotation $\alpha_\lambda$. However, those skilled in the art will recognize that the Brewster's angle reflection results in substantially s-polarized light as indicated in equation (7) by the zeroed p-polarization row of the Brewster's angle Jones matrix $R_B$. This simplified optical geometry permits a simplified and more robust method for determining the polarization rotation $\alpha_\lambda$.

In a preferred embodiment, the glucose level processor 90 measures the polarization rotation $\alpha_\lambda$ as the angular shift of the major axis of the polarization ellipse of the exiting light 54 relative to the s-polarization angle which is perpendicular to the plane of incidence. Optionally, a correction is made for refractive changes due to transmission through the aqueous humor/cornea/ambient interface. The appropriate incident angle $\theta_I$ to obtain the Brewster's angle reflection at the lens 16 is suitably identified by varying the angle of incidence about the nominal value of $\theta_I$ (computed from $\theta_B$ and ocular geometric considerations) to maximize the signal-to-noise ratio. For the listed refractive indices and the exemplary ocular geometry of Le Grand, a suitable nominal angle of incidence relative to the normal to the eye is $\theta_I' = 50.35°$.

Figure 2:
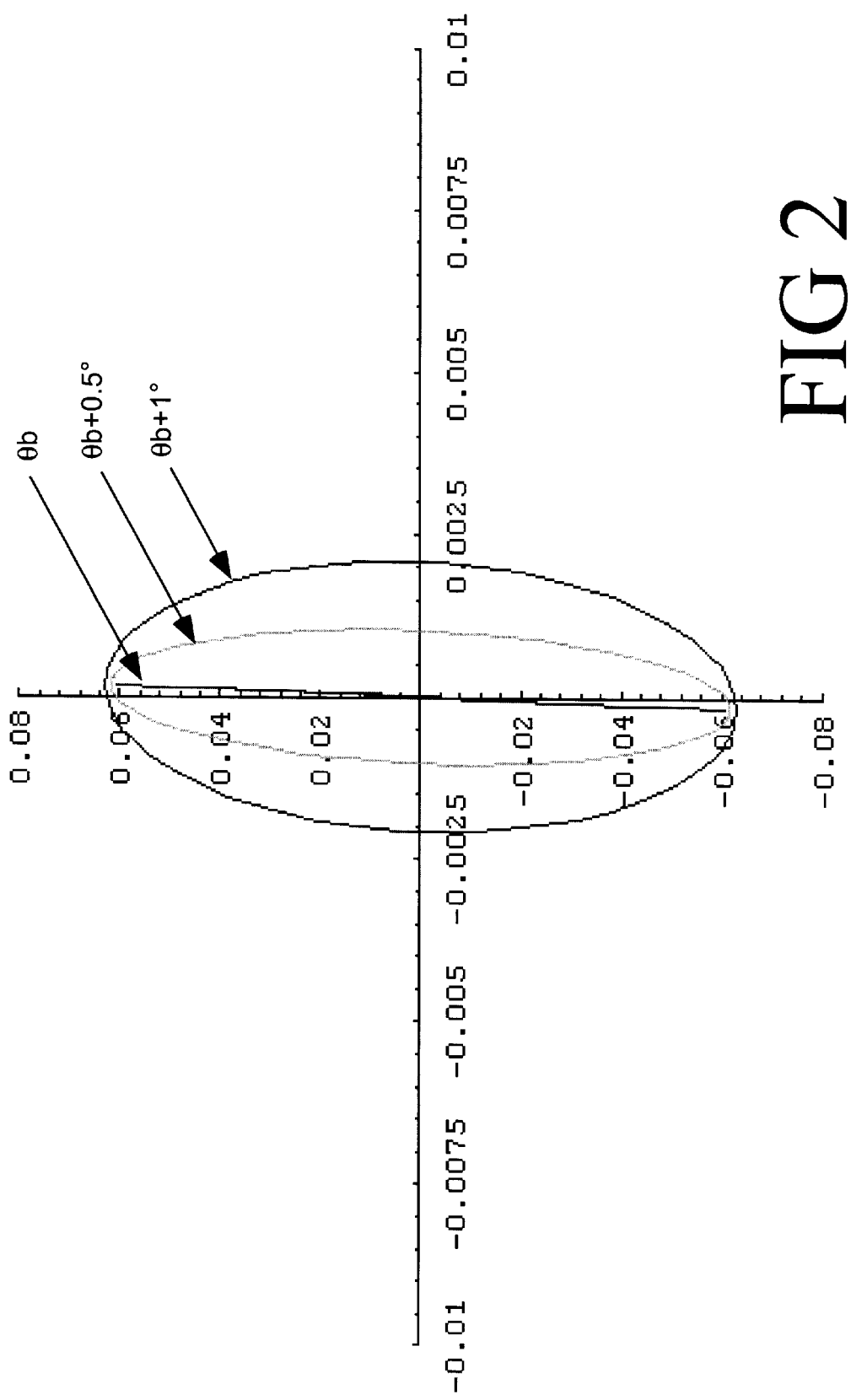
FIG. 2 shows the polarization of the exiting light for incident angles that produce light incident on the ocular lens at the Brewster's angle, at the Brewster's angle plus 0.5°, and at the Brewster's angle plus 1°.

With continuing reference to FIG. 1, and with further reference to FIG. 2, the apparatus 10 is advantageously optically robust. In particular, the angle of incidence can vary significantly without producing substantial error in the determined polarization rotation $\alpha_\lambda$. As seen in FIG. 2, alignment at the Brewster's angle (designated θb in FIG. 2) results in a substantially linearly polarized exiting light 54. A deviation from the Brewster angle has the effect of broadening the polarization from the purely linear polarization into an elliptical polarization due to an increasingly large p-polarization component being retained upon reflection from the lens 16. However, deviations in excess of 1° do not significantly change the rotational orientation of the major axis of the elliptical polarization, which is controlled by the s-polarization component due to the near-Brewster angle reflection.

Figure 3:
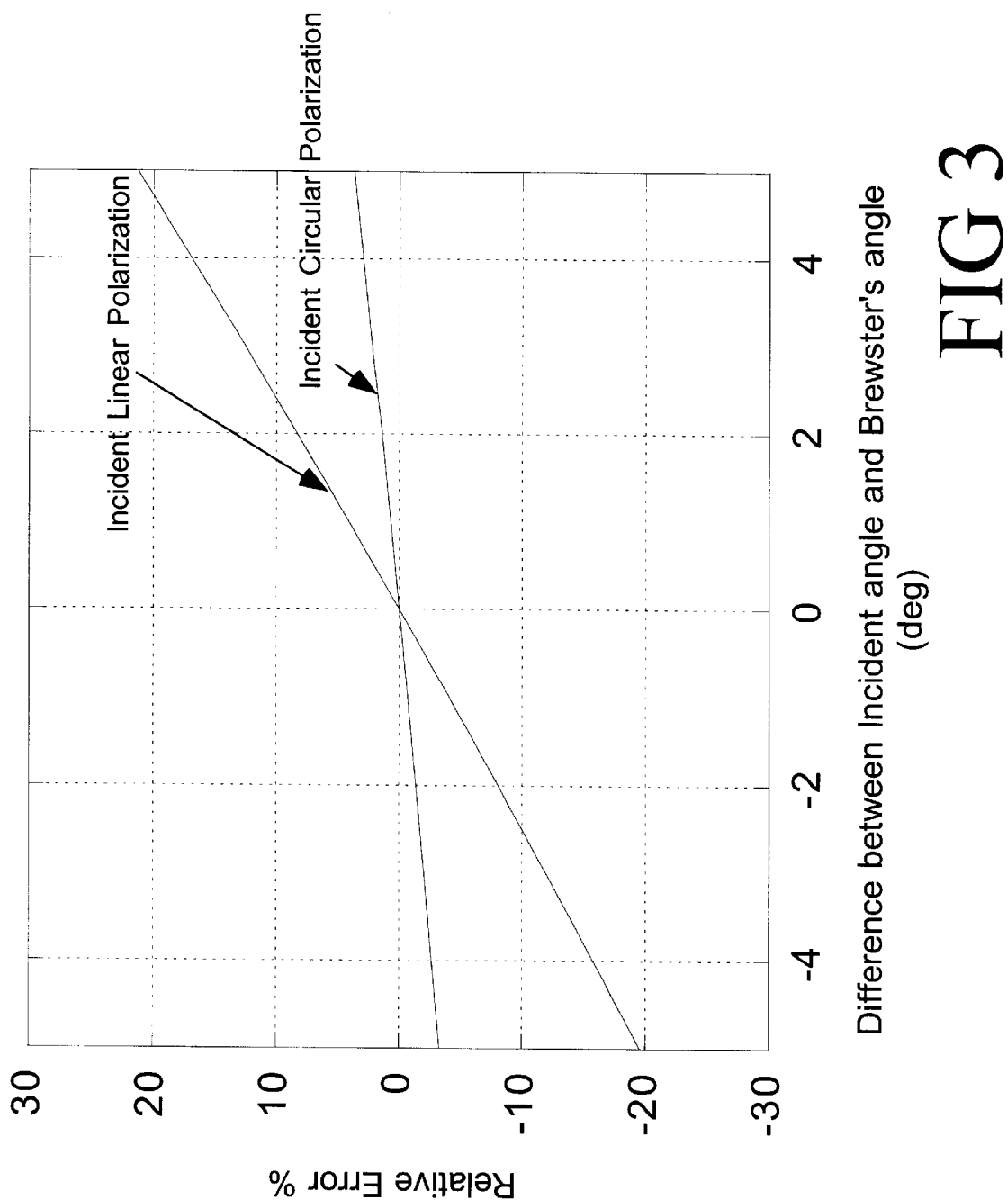
FIG. 3 compares simulated calculations of the percentage error due to deviations from the Brewster's angle of reflection at the lens for an incident circularly polarized beam and an incident linearly polarized beam.

With reference to FIG. 3, simulations indicate that a reduced percentage error is obtained using circularly polarized incident light as compared with incident light that is linearly polarized perpendicular to the incident plane, i.e. s-polarized. As seen in FIG. 3, deviations from the Brewster's angle of up to 4° result in less than a 5% error in the glucose determination. As a result, there is a relatively large tolerance for the angular alignment of the apparatus 10, especially when circularly polarized incident light is employed.

With returning reference to FIG. 1, because the optical activity of glucose in the aqueous humor is substantially larger than that of other optically active substances, a single-wavelength glucose monitoring is contemplated, in which the glucose level processor 90 computes the glucose level from the polarization rotation $\alpha_\lambda$ according to equation (3), in which the index i runs over only a single substance, namely glucose.

Optionally, the effects of confounding optically active substances other than glucose can be corrected for by performing polarization rotation measurements at several wavelengths. Polarization rotation measurements are performed at a number of wavelengths which equals or exceeds the number of significant optically active substances in the aqueous humor 22. Each measured polarization rotation includes a cumulative rotation effect of the several optically active substances. The concentrations of the several optically active substances is computed by the glucose level processor 90 by simultaneously solving equation (3) at the several wavelengths. This multiple-wavelength processing can be expressed in matrix form for the several wavelengths as:

$$\begin{bmatrix} \alpha_{\lambda 1} \\ \alpha_{\lambda 2} \\ \alpha_{\lambda 3} \end{bmatrix} = \begin{bmatrix} [\alpha]^T_{\lambda 1,1} L_{\lambda 1} & [\alpha]^T_{\lambda 1,2} L_{\lambda 1} & [\alpha]^T_{\lambda 1,3} L_{\lambda 1} \\ [\alpha]^T_{\lambda 2,1} L_{\lambda 2} & [\alpha]^T_{\lambda 2,2} L_{\lambda 2} & [\alpha]^T_{\lambda 2,3} L_{\lambda 2} \\ [\alpha]^T_{\lambda 3,1} L_{\lambda 3} & [\alpha]^T_{\lambda 3,2} L_{\lambda 3} & [\alpha]^T_{\lambda 3,3} L_{\lambda 3} \end{bmatrix} \begin{bmatrix} c_1 \\ c_2 \\ c_3 \end{bmatrix} \quad (10)$$

where in equation (10) three optically active substances and polarization rotation measurements at three different wavelengths are assumed. Those skilled in the art can readily modify equation (10) to accommodate additional optically active substances, and/or to accommodate an overdetermined system in which the number of measured wavelengths exceeds the number of optically active substances whose levels are to be computed.

Since serum glucose levels are presently regarded as a standard measure for diabetic monitoring, the glucose level processor 90 optionally includes a suitable adjustment, such as multiplying by a scaling factor, to convert the measured glucose level in the aqueous humor 22 to a serum glucose concentration.

Figure 4:
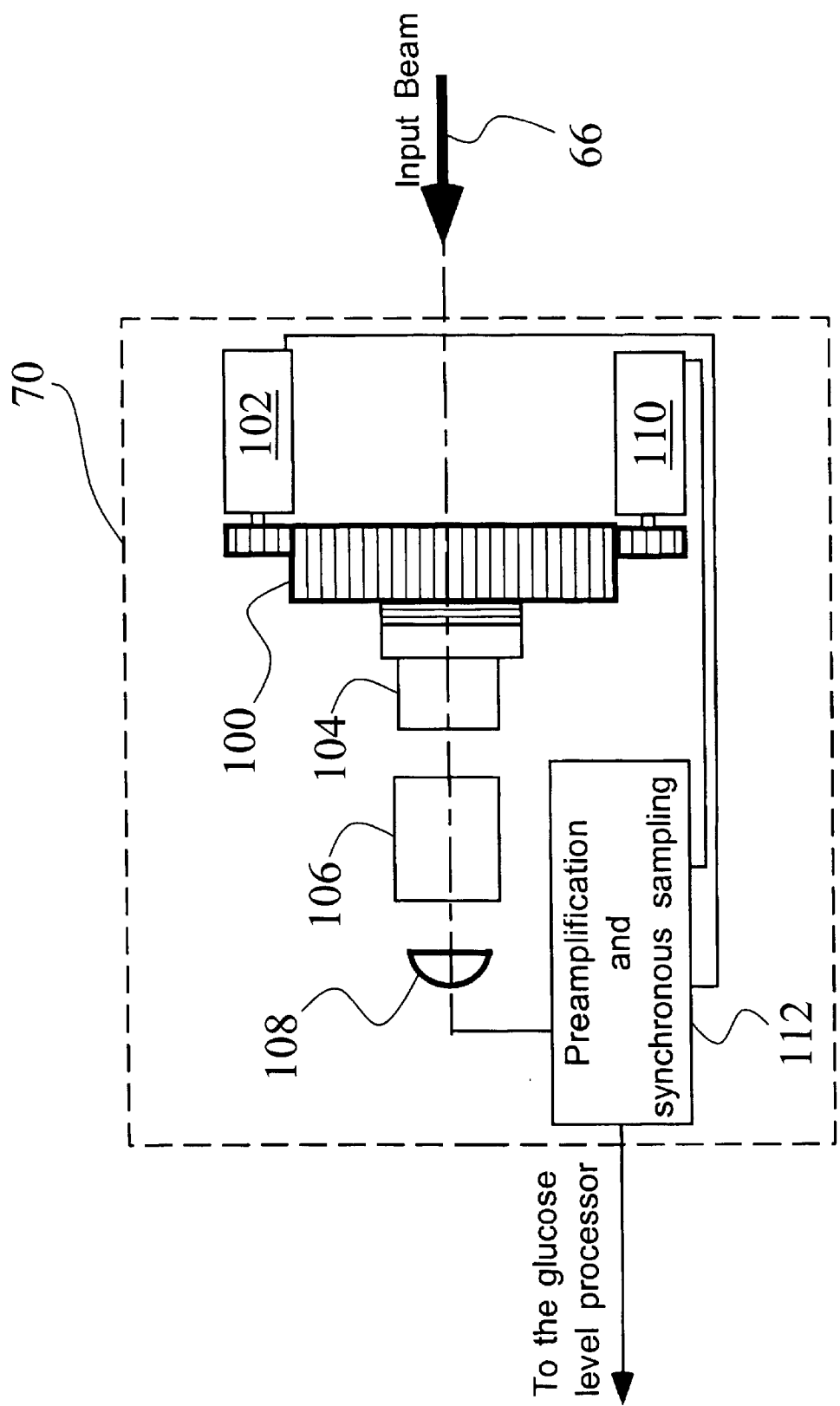
FIG. 4 illustrates an exemplary polarization detector which is suitable for use in the apparatus of FIG. 1.

With reference to FIG. 4, a suitable embodiment of the polarization detector 70 includes rotating wheel 100 and corresponding driving motor 102. A wave retarder 104 is mounted to the rotating wheel 100 and rotates therewith. The wave retarder 104 cooperates with a stationary linear polarizer 106, such as a Glan-Thompson polarizer, to convert the polarization of the second beam 66 into a periodic intensity modulation that is detected by a photodiode 108 or other photodetector. An optical encoder 110 provides an electronic measurement of the rotational frequency of the rotating wheel 100, which is used by a preamplification and synchronous sampling circuit 112 to perform a synchronous sampling of the signal detected by the photodiode 108. In order to consider an integer number of revolution periods of the rotating optical component 104, the optical encoder 110 should provide a digital signal pulse when the rotating wheel 100 assumes a selected angular position.

With θ denoting the rotation angle with respect to a given reference frame, the Muller matrix of the wave retarder 104 is given by:

$$WR(\theta) = \begin{bmatrix} 1 & 0 & 0 & 0 \\ 0 & \cos^2 2\theta + \sin^2 2\theta \cos 2\chi & 1/2 \sin 4\theta (1-\cos 2\chi) & -\sin 2\theta \sin 2\chi \\ 0 & 1/2 \sin 4\theta (1-\cos 2\chi) & \sin^2 2\theta + \cos^2 2\theta \cos 2\chi & \cos 2\theta \sin 2\chi \\ 0 & \sin 2\theta \sin 2\chi & -\cos 2\theta \sin 2\chi & \cos 2\chi \end{bmatrix} \quad (11)$$

where $\chi = \pi/\lambda L(n_y - n_x)$ and $n_y$ and $n_x$ the refractive indices of the retarder. The Muller matrix of the Glan-Thompson linear polarizer 106 is:

$$P = \begin{bmatrix} 1 & 1 & 0 & 0 \\ 1 & 1 & 0 & 0 \\ 0 & 0 & 0 & 0 \\ 0 & 0 & 0 & 0 \end{bmatrix} \quad (12)$$

The optical power detected by the photodiode 108 is:

$$p(\theta) = [1 \ 0 \ 0 \ 0] \cdot P \cdot WR(\theta) = \frac{1}{4}(2S_0 + S_1(1+\cos(2\chi)) + \quad (13)$$

$$\frac{1}{4}S_1(1-\cos(2\chi))\cos 4\theta +$$

$$\frac{1}{4}S_2(1-\cos(2\chi))\sin 4\theta +$$

$$\frac{1}{4}S_3 \sin 2\chi \sin 2\theta$$

where $S = [S_0 \ S_1 \ S_2 \ S_3]$ is the Stokes vector of the input beam. Hence, the Stokes parameters are extracted from the Fourier coefficients of $p(\theta)$ according to:

$$\frac{1}{4}(2S_0 + S_1(1+\cos(2\chi))) = \frac{1}{n\pi} \int_0^{n\pi} p(\theta) d\theta \quad (14)$$

-continued $$\frac{1}{4}S_1(1-\cos(2\chi)) = \frac{1}{n\pi}\int_0^{n\pi} p(\theta)\cos 4\theta\, d\theta$$

$$\frac{1}{4}S_2(1-\cos 2\chi)) = \frac{1}{n\pi}\int_0^{n\pi} p(\theta)\sin 4\theta\, d\theta$$

$$\frac{1}{4}S_3\sin 2\chi = \frac{1}{n\pi}\int_0^{n\pi} p(\theta)\sin 2\theta\, d\theta$$

Using the synchronizing signals generated by the optical encoder 110, the four integrals of equation (14) are numerically calculated by the glucose level processor 90 using the samples of the signal p(θ). The parameter $S_O$ is proportional to the intensity of the wave.

The polarization rotation angle (α) that characterizes the glucose concentration corresponds to the orientation of the major axis of the ellipse of polarization, and is computed by the glucose level processor 90 according to:

$$\alpha = \frac{1}{2}\arctan\left(\frac{S_2}{S_1}\right) \quad (15)$$

The ellipticity of the of polarization ellipse is suitably characterized by an ellipticity angle (φ) given by:

$$\phi = \frac{1}{2}\arcsin\left(\frac{S_3}{S_0}\right) \quad (16)$$

In the absence of birefringence effects and alignment errors, the ellipticity angle should be zero corresponding to a linear polarization. The contribution of randomly polarized components, due for example to scattering, is optionally extracted and represented by a polarization coefficient (pc) given by:

$$pc = \sqrt{\frac{S_1^2 + S_2^2 + S_3^2}{S_0^2}} \quad (17)$$

The polarization coefficient provides a convenient index of the quality of the polarization rotation measurement.

The polarization detector 70 shown in FIG. 4 is exemplary only. Those skilled in the art can readily select or construct other polarization analyzers that suitably measure the polarization rotation angle of the exiting light 54.

Figure 5:
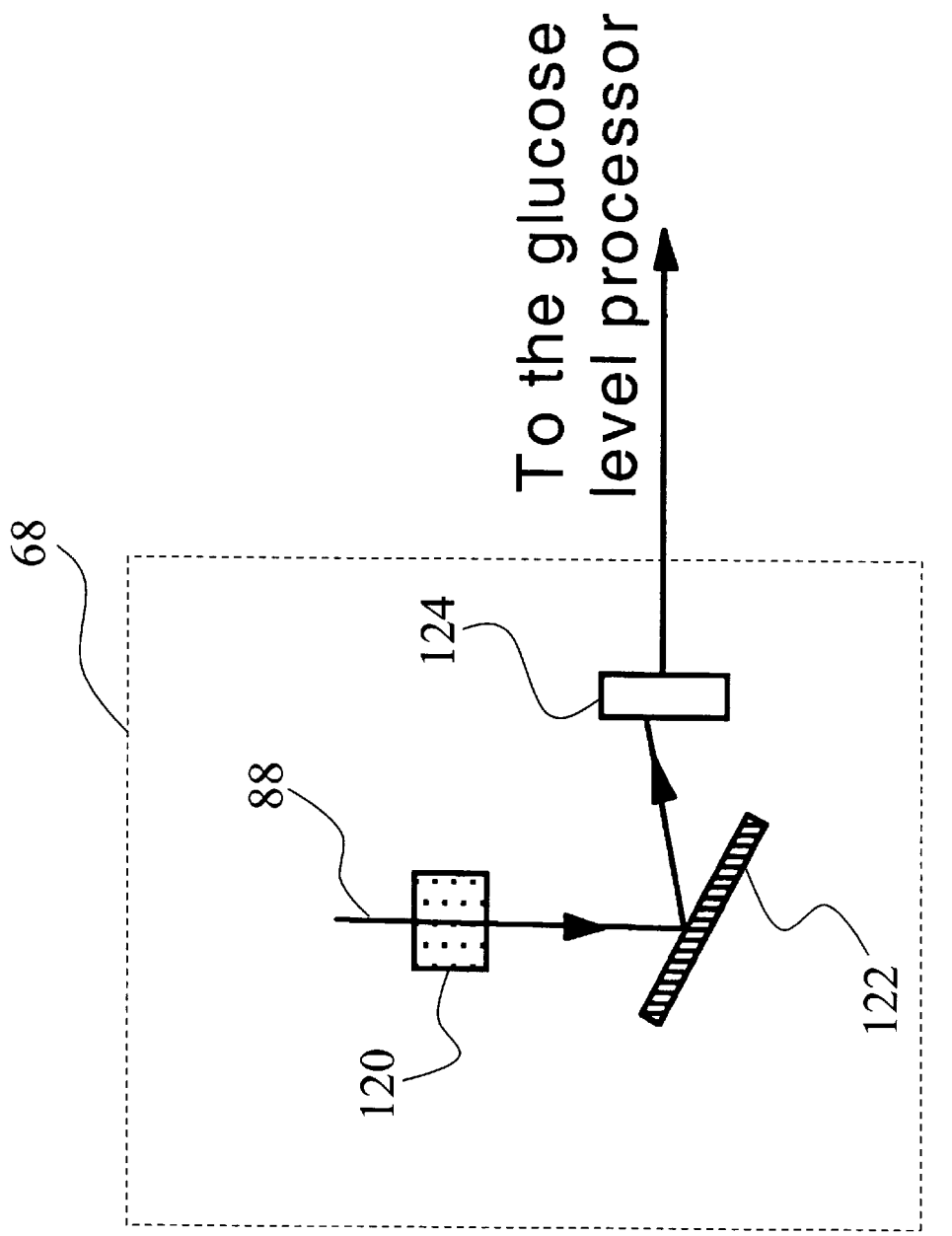
FIG. 5 illustrates an exemplary low-coherence interferometric detector which is suitable for use in the apparatus of FIG. 1.

With reference to FIG. 5, a suitable embodiment of the path length detector 68 includes a polarizer 120, a dispersive grating 122, and a linear detector array 124, which is suitably a linear camera employing a charge-coupled device (CCD). The detector 68 operates substantially similarly to a Michelson interferometer. The interference phase φ(ν) of the light dispersed by the grating 122 is given by:

$$\phi(\nu) = \frac{4\pi}{c}L\nu \quad (18)$$

where ν is the optical frequency, L is the optical path length difference, and c is the speed of light.

Figure 6:
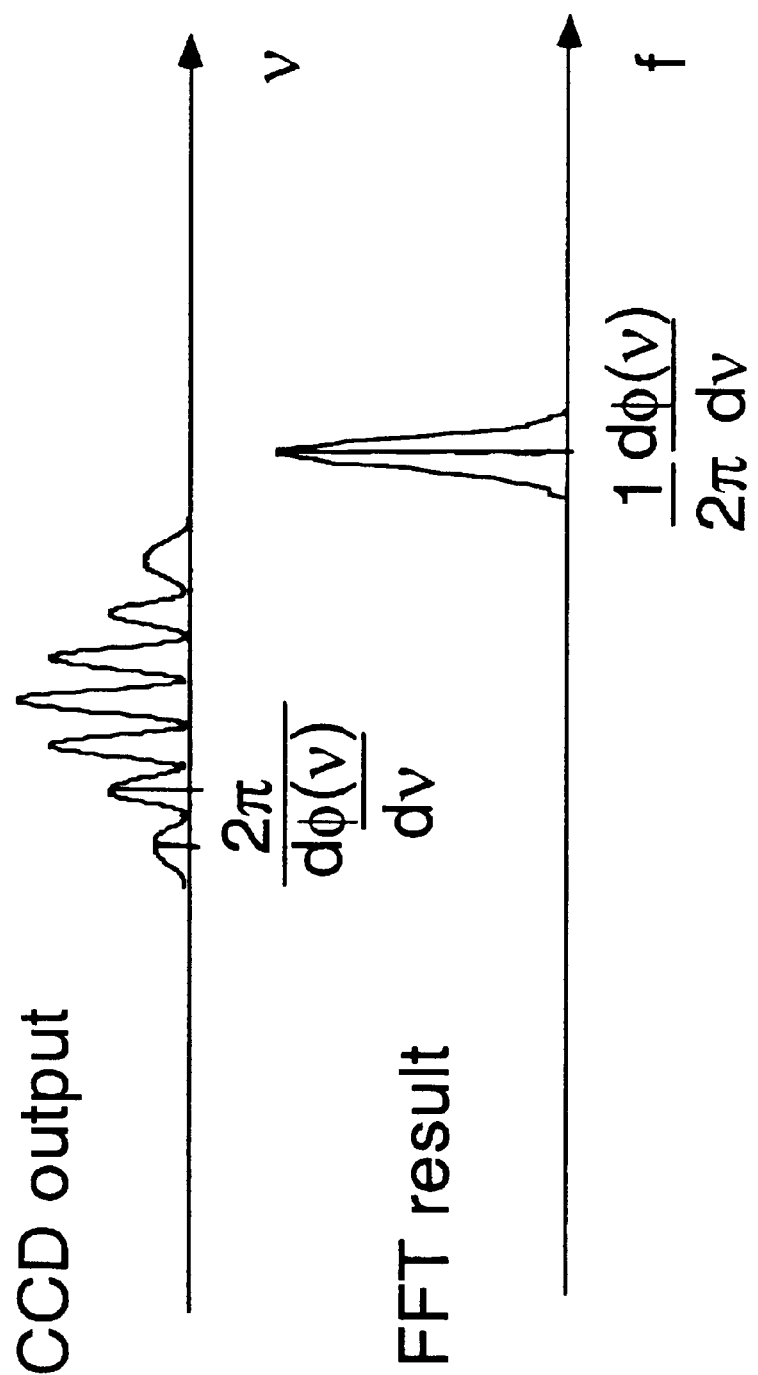
FIG. 6 schematically shows a fast-Fourier transform (FFT) analysis with respect to optical frequency of the output of the charge-coupled device (CCD) component of the low-coherence interferometric detector of FIG. 5.

With reference to FIG. 6, a fast-Fourier transform (FFT) analysis with respect to the optical frequency of the output of the CCD 124 provides the first derivative of φ(ν) from which the optical path difference L can be extracted in accordance with equation (18).

The low-coherence interferometric detector 68 described with reference to FIGS. 5 and 6 is exemplary only, and those skilled in the art can construct other suitable optical arrangements for measuring the optical path difference.

Figure 7:
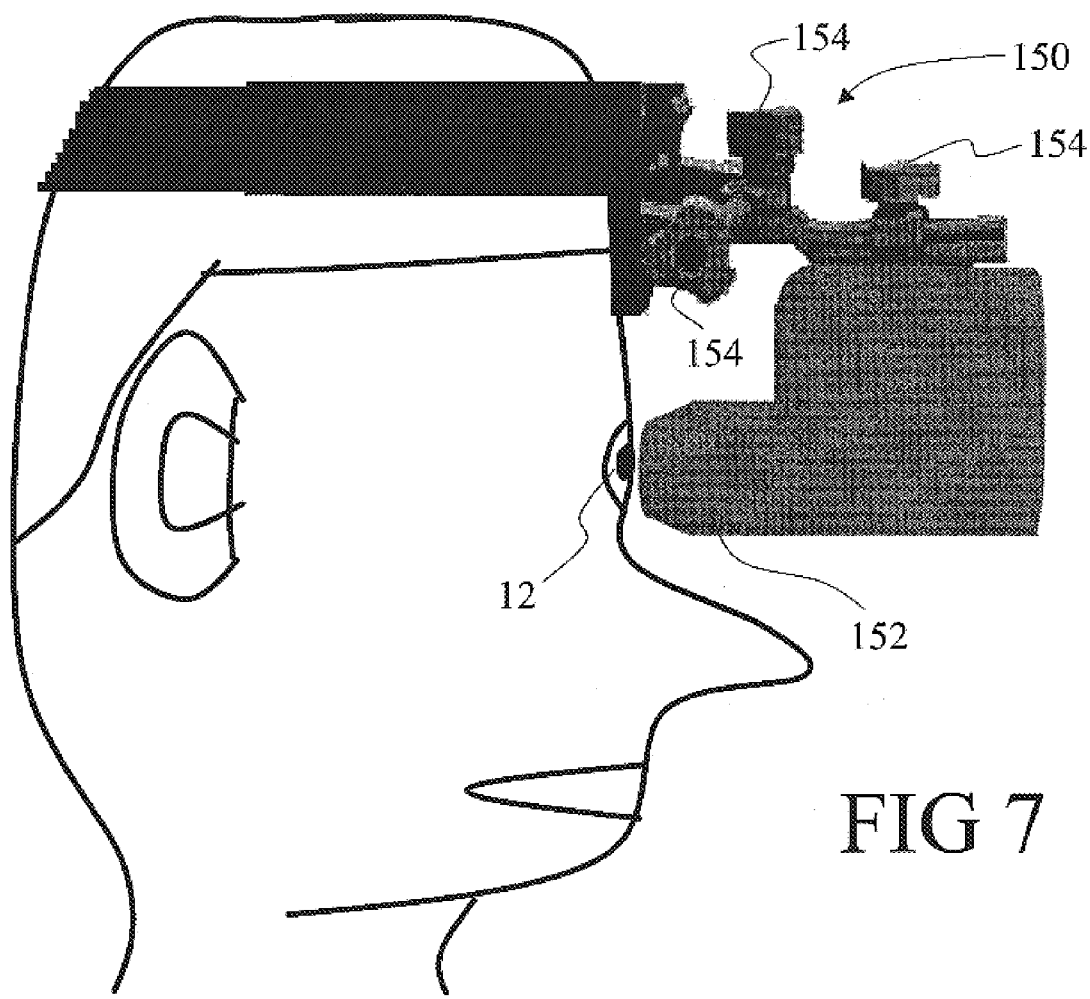
FIG. 7 diagrammatically shows an exemplary headband head mounting of the apparatus of FIG. 1.
Figure 8:
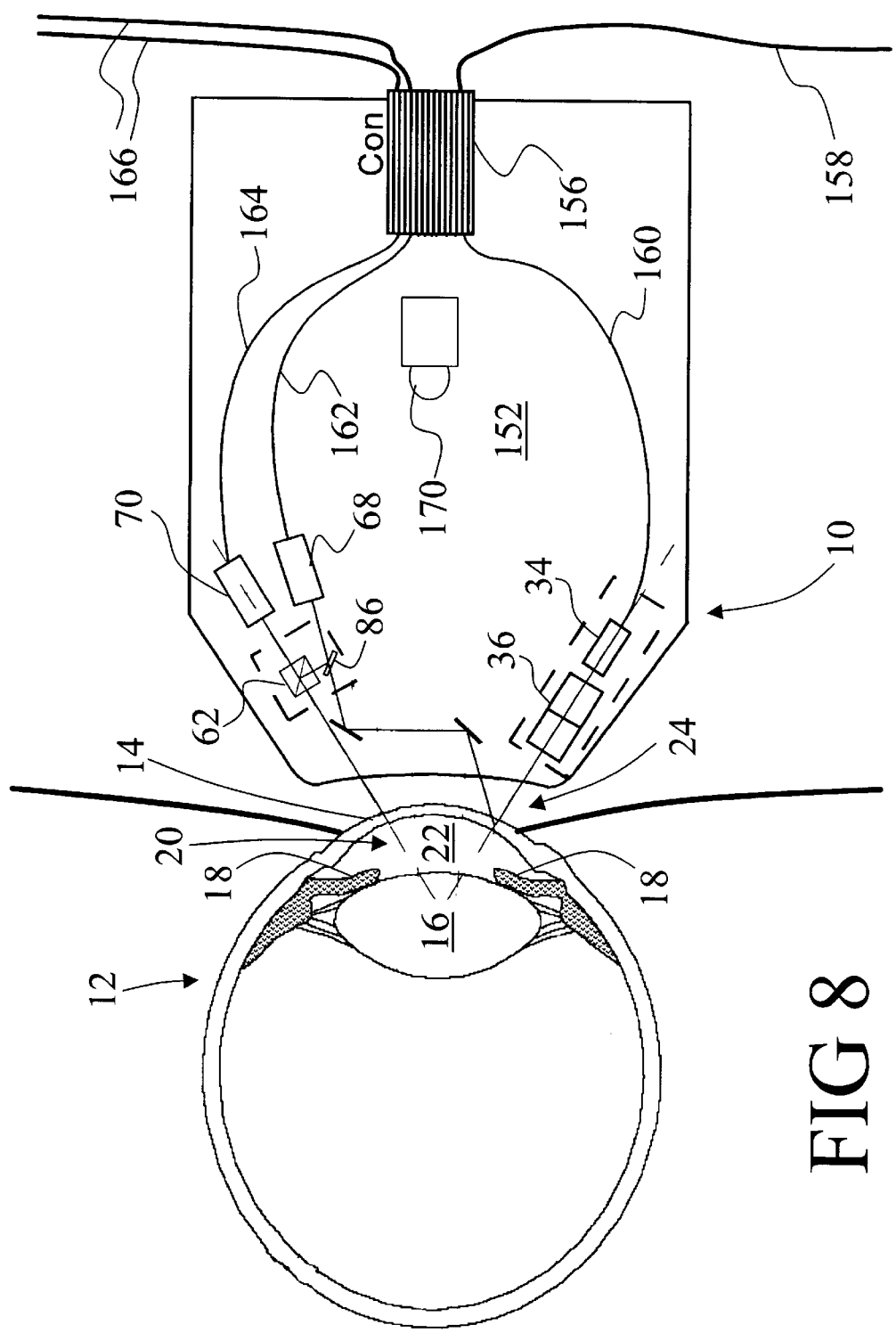
FIG. 8 shows an enlarged view of the substrate of the headband head mount of FIG. 7, which enlarged view diagrammatically illustrates a suitable arrangement of optical components thereon.

With reference to FIGS. 7 and 8, the apparatus 10 is preferably arranged on a rigid head mount such as a headband 150 that rigidly positions a substrate 152 in close proximity to the monitored eye 12. As best seen in FIG. 8, the apparatus 10 is arranged on the substrate 152. The headband 150 includes adjustment knobs 154 that adjust for the subject's head size and enable the substrate 152 to be positioned relative to the eye 12 of interest. Because of the weak sensitivity of the polarization rotation measurement to small deviations from the Brewster's angle as described previously with particular reference to FIGS. 2 and 3, the headband 150 typically does not require a special angular adjustment beyond the positioning knobs 154. Optionally, however, a dedicated angular adjustment for the substrate 152 or for optical components arranged thereon is provided.

The apparatus 100 on the substrate 152 suitably employs fiber optical connections. In particular a multiplexor 156 connects with an input optical fiber 158 which delivers light from the light source 30. An optical fiber 160 delivers the source light from the multiplexor 156 to the first optical component 34 of the apparatus 10. Wires 162, 164 deliver the outputs of the low-coherence interferometric detector 68 and the polarization analyzer 70, respectively, to the multiplexor 156, and wires 166 carry the outputs of the detectors 68, 70 off the substrate 152. Optionally, selected elements such as the transducive and electrical elements 108, 112, 124 of the detectors 68, 70 are arranged remotely from the substrate 152, in which arrangement the electrical wires 162, 164, 166 are selectively replaced by fiber optical connections that carry optical signals to the transducers 108, 124.

To minimize eye movement or discomfort for the subject during the glucose level measurement, a fixating light source 170 is preferably arranged on the substrate 152. The fixating light source 170 is suitably embodied as a flashing light emitting diode (LED), and is arranged in front of the eye 12 to distract the subject from the incident light produced by the apparatus 10 and to keep the eye 12 focused at a fixed orientation during the glucose level measurement. The arrangement of the fixating light source 170 also prevents optical interference of the apparatus 10 by the fixating light source 170.

Instead of the illustrated headband 150, a helmet or other apparatus which rigidly mounts to the subject's head can be used. A head-mounted arrangement is particularly suitable for self-monitoring. However, it is also contemplated to employ the apparatus 10 in a medical setting such as a doctor's examination room or the like. In such a setting, the apparatus 10 can be arranged on a table, chair, or other support. The patient's head is rigidly affixed to the table, chair, et cetera such that a well-defined incident angle $\theta_I'$ is established.

It is known in the art that the cornea exhibits birefringence at oblique angles of incidence such as are employed in the embodiment shown in FIGS. 1 and 8. The corneal birefringence can introduce an additive retardation or ellipticity of the polarization which can affect the glucose concentration measurement. The corneal birefringence is suitably addressed by calibrating the apparatus 10 with respect to a measured serum glucose level, e.g. obtained through a finger-stick blood test. The calibration is preferably performed for a selected incident plane of the apparatus 10 with respect to the eye. Two or more calibration measurements at different blood glucose concentrations are preferably performed to generate a glucose calibration over a suitable range of glucose levels. The calibration versus a serum glucose measurement is preferably repeated periodically, e.g. once every 6 months. The calibration curve is specific to the patient and to the selected incident plane orientation.

Figure 9:
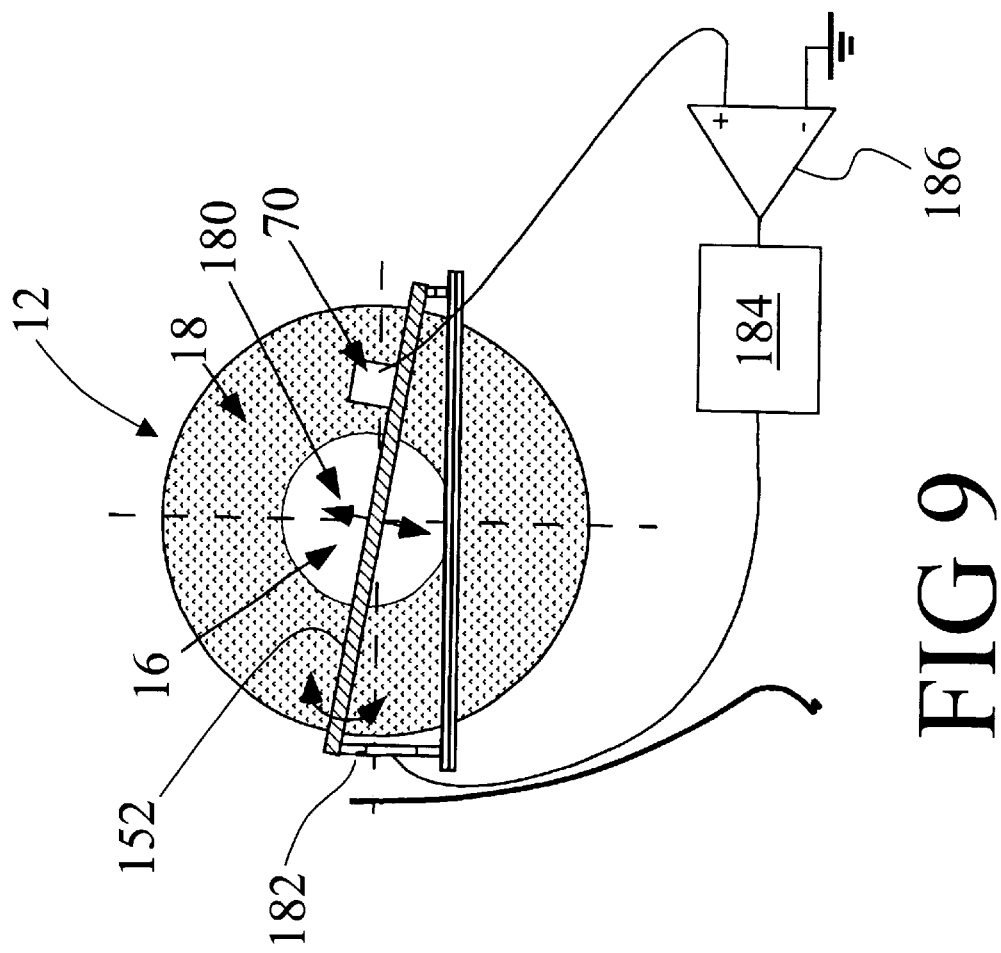
FIG. 9 diagrammatically illustrates an apparatus for compensating for corneal birefringence.

With reference to FIG. 9, another suitable method for addressing the corneal birefringence is described, in which an orientation of the substrate 152 (which corresponds to an orientation of the incident plane, i.e. the plane containing the incident and reflected light beams 50, 52) is adjusted to minimize the effect of the corneal birefringence on the glucose level measurement. It is known that the corneal birefringence is substantially uniaxial, and is characterized by a slow axis 180 directed along an upper-temporal to lower-nasal direction.

The orientation of the substrate 152 is mechanically adjusted, e.g. using a piezoactuator 182 operated by a driver 184 to orient the polarization of the reflected light 52 along one of the birefringence axes of the cornea 14. When so oriented, the retardation introduced by the corneal birefringence is null. At the output of the polarimetric sensor 70, the ellipticity angle φ given by equation (16) above contains information about the ellipticity of the polarization of the probe beam. To find the orientation of the substrate 152 that nulls the corneal birefringence effects, the polarization ellipticity of the exiting beam 54 is monitored by a feedback element 186 which communicates with the driver 184 to adjust the orientation of the substrate 152 until the ellipticity of the exiting beam 54 is minimized, corresponding to an optimum substrate 152 orientation which minimizes corneal birefringence effects. The glucose measurement is then performed at the selected optimum substrate 152 orientation.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A method for determining a diagnostic glucose level for a person, the method comprising:

reflecting light off an ocular lens at a Brewster's angle to produce an initial linear polarization of reflected light;

measuring a polarization rotation of the reflected light after exiting the eye, the polarization rotation being measured with respect to the initial linear polarization; and determining a glucose concentration based on the measured polarization rotation.

2. The method as set forth in claim 1, wherein the reflecting step includes:

adjusting a light source incident angle to maximize a signal-to-noise ratio.

3. The method as set forth in claim 1, wherein the reflecting step includes:

reflecting circularly polarized light off the ocular lens at the Brewster's angle of an aqueous humor/lens interface.

4. The method as set forth in claim 1, wherein the measuring step includes:

interferometrically measuring an optical path length through an ocular aqueous humor, the measured optical path length being used in the determining of a glucose concentration.

5. The method as set forth in claim 1, wherein the measuring step includes:

determining a major axis of an elliptical polarization of the reflected light after exiting the eye, the polarization rotation corresponding to a rotation of major axis.

6. The method as set forth in claim 1, wherein the steps of reflecting light and measuring a polarization rotation are repeated for a plurality of wavelengths, and the step of determining the glucose level based on the measured polarization rotation includes:

determining levels for a plurality of optically active substances including glucose in the aqueous humor based on the measured polarization rotations at the plurality of wavelengths.

7. A method for determining a diagnostic glucose level, the method comprising:

reflecting light from an internal ocular interface at an incident angle that has a selected reflection polarization characteristic;

measuring an elliptical polarization of the reflected light; and computing a glucose concentration based on a polarimetric rotation parameter derived from the measured elliptical polarization of the reflected light and the selected reflection polarization characteristic.

8. The method as set forth in claim 7, wherein the incident angle is a Brewster's angle.

9. The method as set forth in claim 7, wherein the internal ocular interface includes an ocular lens surface.

10. The method as set forth in claim 9, wherein the incident angle is within about an eight angular degree range centered about a Brewster's angle of an aqueous humor/lens interface.

11. The method as set forth in claim 7, wherein the measuring step includes:

measuring a polarization of the reflected light;

correcting the measured polarization for refractive polarization changes occurring at selected ocular interfaces; and determining a polarization rotation computed based on the corrected measured polarization and the selected reflection polarization characteristic.

12. The method as set forth in claim 7, further including:

adjusting a plane of incidence of the reflecting from the internal ocular interface to minimize an ellipticity produced by an ocular birefringence.

13. A method for determining a diagnostic glucose level, the method comprising:

reflecting light from a lens/vitreous humor interface at a critical angle for total reflection at the lens/vitreous humor interface;

measuring a polarimetric parameter of the reflected light; and computing a glucose concentration based on the polarimetric parameter.

14. A method for determining at least a diagnostic glucose level, the method comprising:

reflecting light from an internal ocular interface at an incident angle that has a selected reflection polarization characteristic;

measuring a polarimetric parameter of the reflected light;

repeating the reflecting and measuring steps for light at a plurality of wavelengths to obtain a plurality of polarimetric parameters;

computing polarization rotation values at each of the plurality of wavelengths; and determining compositions of a plurality of optically active substances including glucose based on the plurality of polarization rotation values.

15. An apparatus for determining a diagnostic glucose level in a human subject, the apparatus comprising:
   a light source that produces collimated light at a selected wavelength, the collimated light arranged such that the collimated light passes through a portion of an eye of the subject and reflects off an eye lens at a selected angle as reflected light;
   a polarization analyzer that measures a polarization of the reflected light that exits the eye;
   a path length processor that determines an optical path length of the reflected light within an aqueous humor of the eye; and
   a glucose level processor that computes a glucose concentration based on the measured polarization and the determined optical path length.

16. The apparatus as set forth in claim 15, wherein the selected angle is a Brewster's angle, and the glucose level processor computes the glucose concentration based on polarization characteristics of the Brewster's angle reflection.

17. The apparatus as set forth in claim 15, wherein the light source is selected from a group consisting of:
   a white light source with one or more filter elements that spectrally filter light produced by the white light source,
   an arc discharge lamp,
   one or more light emitting diodes, and
   a multiple-wavelength laser.

18. The apparatus as set forth in claim 15, further including:
   a polarizer that polarizes light produced by the light source prior to entering the eye.

19. The apparatus as set forth in claim 15, wherein the path length processor includes:
   an interferometric detector that measures a difference in optical path length between the collimated light after reflection from the eye lens and a reference beam derived from the light source.

20. The apparatus as set forth in claim 15, further including:
   a head mount that fastens to a head of the subject and supports at least the polarization analyzer and the path length detector.

21. The apparatus as set forth in claim 15, further including:
   a substrate on which the collimated light, the polarization analyzer, and the path length detector are arranged;
   an actuator that operates on the substrate to adjust a substrate orientation with respect to the eye; and
   a feedback circuit incorporating an output of the polarization analyzer, the feedback circuit driving the actuator to arrange the substrate at a selected substrate orientation that minimizes an ocular birefringence.

* * * * *